(12) United States Patent
Mezzoli

(10) Patent No.: US 6,902,557 B2
(45) Date of Patent: Jun. 7, 2005

(54) DEVICE FOR RECTAL LAVAGE

(76) Inventor: Giorgio Mezzoli, Via Ricci Curbastro, 56/1 - 48022 Lugo (Prov. of RAVENNA) (IT)

(*) Notice: Subject to any disclaimer, the term of this patent is extended or adjusted under 35 U.S.C. 154(b) by 170 days.

(21) Appl. No.: 10/169,302

(22) PCT Filed: Dec. 20, 2000

(86) PCT No.: PCT/EP00/13011
§ 371 (c)(1),
(2), (4) Date: Sep. 9, 2002

(87) PCT Pub. No.: WO01/49345
PCT Pub. Date: Jul. 12, 2001

(65) Prior Publication Data
US 2003/0114834 A1 Jun. 19, 2003

(30) Foreign Application Priority Data
Dec. 30, 1999 (IT) .......................... M199A2750

(51) Int. Cl.⁷ ............................................. A61M 31/00
(52) U.S. Cl. ....................................... 604/514; 604/911
(58) Field of Search ................................ 604/514, 515, 604/516, 517, 93.01, 911; D24/112, 115, 141, 111, 117

(56) References Cited

U.S. PATENT DOCUMENTS

| | | | | |
|---|---|---|---|---|
| D22,510 S | * | 6/1893 | Hartz | D24/112 |
| D22,669 S | * | 8/1893 | Treverton | D24/112 |
| D29,765 S | * | 12/1898 | Sullivan | D24/112 |
| 2,333,383 A | * | 11/1943 | Klarchuk | 604/275 |
| 2,474,188 A | * | 6/1949 | Pohl | 604/174 |
| 2,541,520 A | * | 2/1951 | Kegel | 600/591 |
| 2,554,068 A | * | 5/1951 | Sokolik | 604/279 |
| 2,921,580 A | * | 1/1960 | Indelicato | 128/838 |
| 3,010,454 A | * | 11/1961 | Lucie et al. | 604/24 |
| D197,795 S | * | 3/1964 | Friedman | D7/669 |
| 3,180,334 A | | 4/1965 | Glenn | 128/245 |
| 3,459,175 A | * | 8/1969 | Miller | 600/431 |
| 3,575,160 A | | 4/1971 | Vass | 128/2 R |
| 3,889,676 A | * | 6/1975 | Greene | 604/101.05 |
| 4,068,663 A | * | 1/1978 | D'Alessandro | 604/200 |
| 4,321,920 A | * | 3/1982 | Gillig | 604/28 |
| 4,419,099 A | * | 12/1983 | Miller | 604/275 |
| 4,943,285 A | | 7/1990 | Hawks | 604/275 |
| 5,197,950 A | * | 3/1993 | Clayton | 604/28 |

* cited by examiner

Primary Examiner—Sharon Kennedy
(74) Attorney, Agent, or Firm—Abelman, Frayne & Schwab

(57) ABSTRACT

Device for rectal lavages consisting of a flexible container (1) containing the washing liquid, a flexible tube (2) and a nozzle (3) equipped with an elongated egg-shaped body (6) from which an upper elongated portion (7) and a concave surface (8) depart, the upper portion (7) being equipped with at least one opening (9), and a concave surface (8) with two tongues (4) of slightly upwards curved shape.

3 Claims, 4 Drawing Sheets

DEVICE FOR RECTAL LAVAGE

REFERENCE TO RELATED APPLICATIONS

This application is a 35 U.S.C. §371 filing of PCT/EP00/13011, filed Dec. 20, 2000.

FIELD OF THE INVENTION

The present invention relates to a device for the rectal wash or irrigation.

PRIOR ART

The inner surface of the terminal portion of the rectum, called the perineal rectum, is characterized by a series of longitudinal and transverse folds suitable to contain the fecal material waiting for the evacuation. The whole area, expecially close to the anal orifice, consists of a highly vascularized mucosa which, in consideration of the function of the organ, may easily incur inflammatory phenomena, especially against the venas haemorrhoidales. Anyway the need to maintain a correct health status of the area does not only concern the general well-being of the individual. In fact, just in consideration of the high vascularization, the perineal portion forms a site of administration of drugs which may provide a degree of absorption comparable to the parenteral administration.

On the market there are various defences useful either to the cleaning of the terminal tract of the rectum, or to stimulate a lazy evacuation and thereby to empty and lighten the perineal area from the waste material possible cause of local irritations and inflammations.

The prior art devices provide for the use of generally complex devices, usually including electrical parts, and therefore of considerable cost, and moreover cumbersome for a domestic use and of complicated use for the average user. Furthermore these devices often take marginally into account the anatomical conformation of the organ being treated.

SUMMARY OF THE INVENTION

Now we have surprisingly found a kind of device for rectal lavages suitable to any size and conformation of the organ, of contained price and easy use, allowing to carry out the cleansing of the rectal channel easily and without wetting the hands.

Figures 2B, 2C:
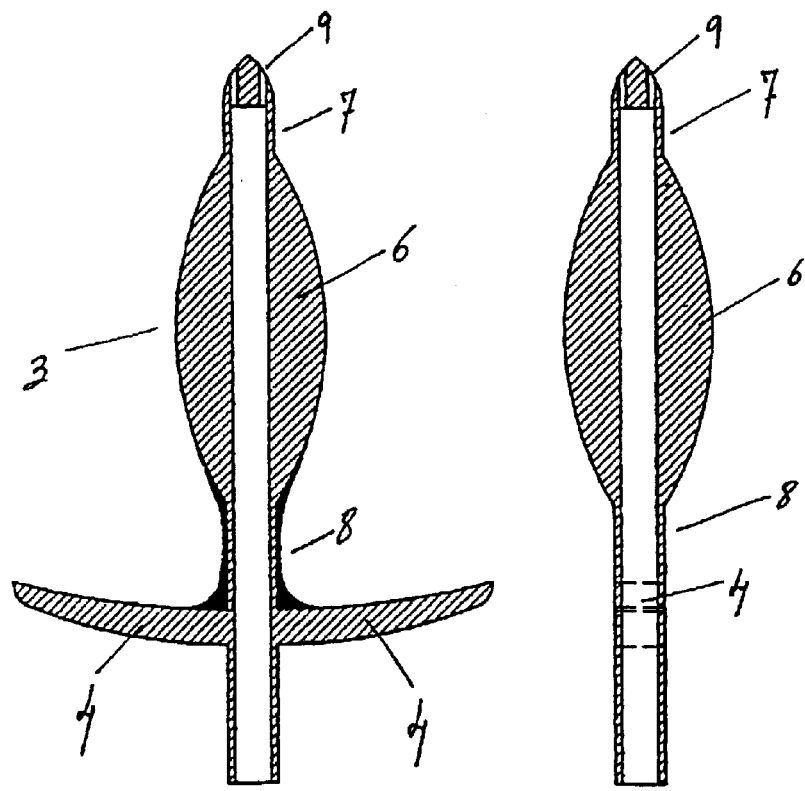
Figure 2A:
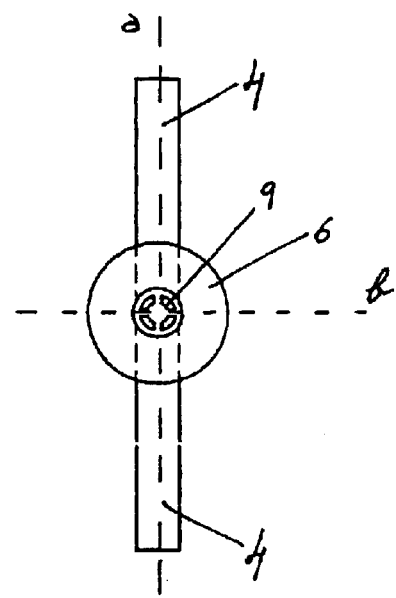

The FIGS. 2a, 2b and 2c show a form of embodiment of the nozzle of the device of the present invention, respectively, from above and in the longitudinal section along the a—a and b—b planes of the FIG. 2a.

Figures 3B, 3C:
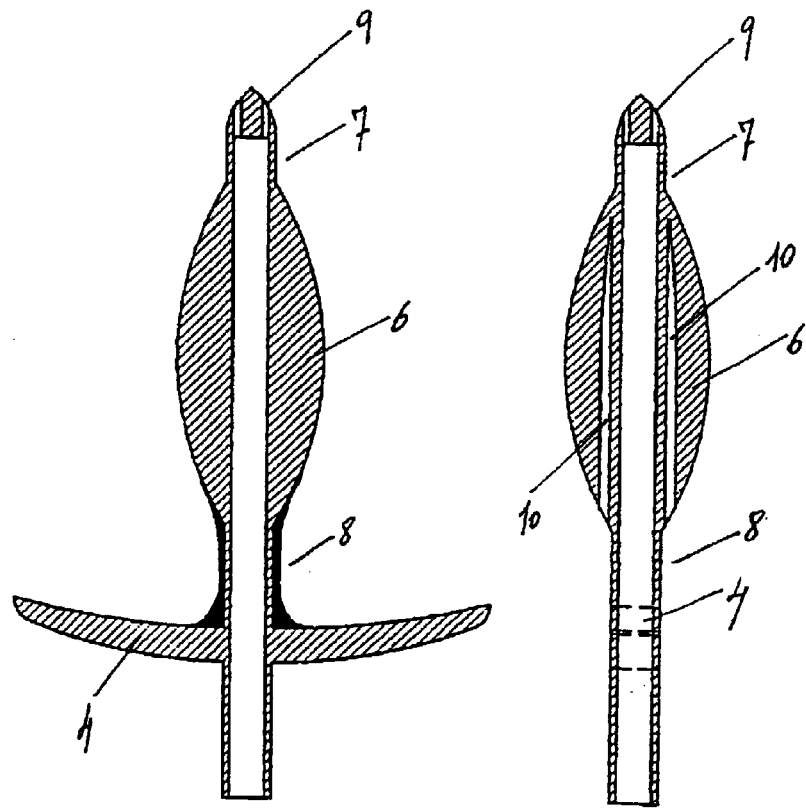
Figure 3A:
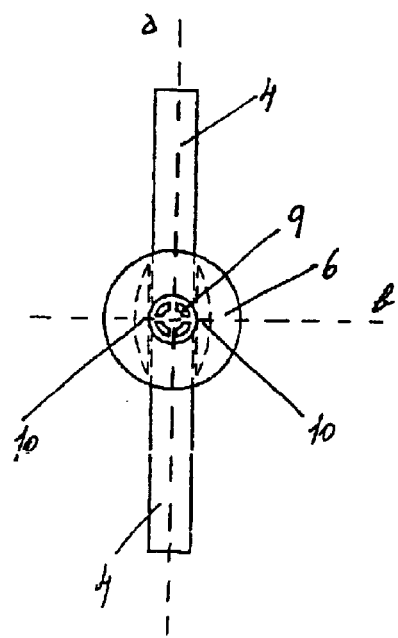

The FIGS. 3a, 3b and 3c show another form of embodiment of the nozzle of the device of the present invention, respectively, from above and in the longitudinal section along the a—a and b—b planes of the FIG. 3a.

Figure 4A:
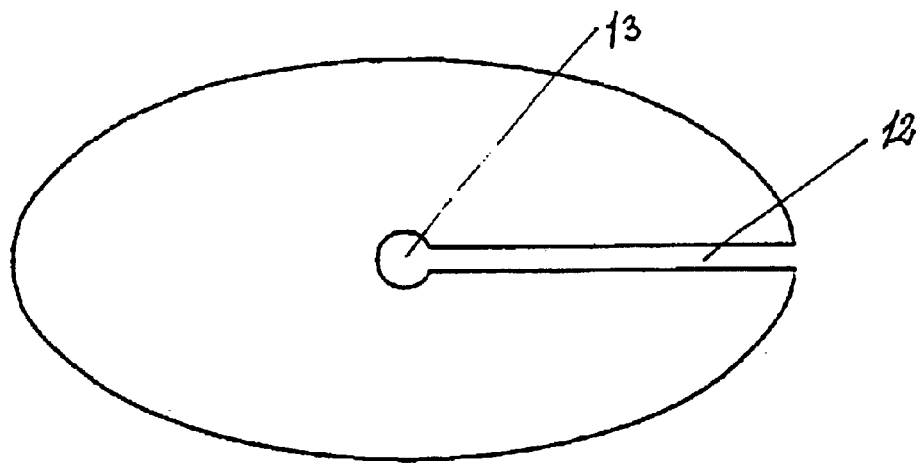
Figure 4B:
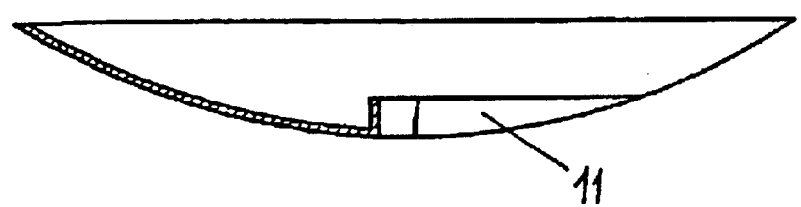
Figure 4C:
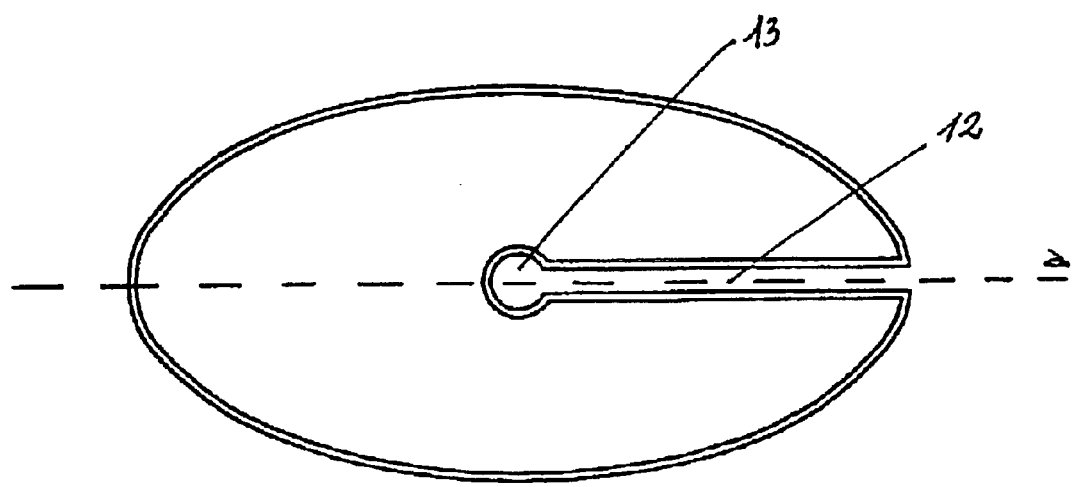

The FIGS. 4a, 4b and 4c show, respectively, a view from below, a longitudinal section along the major axis (a) and a view from above of the disk or cup (5).

DESCRIPTION OF THE INVENTION

The device for rectal ravages of the present invention consists of a flexible container (1) containing the washing liquid, a flexible tube (2) and a nozzle (3) equipped with an elongated egg-shaped body (6) from which an upper elongated portion (7) and a concave surface (8) depart, the upper portion (7) being characterized by at least one opening (9), and the concave surface (8) by two tongues (4) of slightly upwards curved shape.

Optionally the tube (2) is equipped with a disk or cup (5) preferably removable, movable and smooth-running on the tube (2), and coaxial to it.

Figure 1:
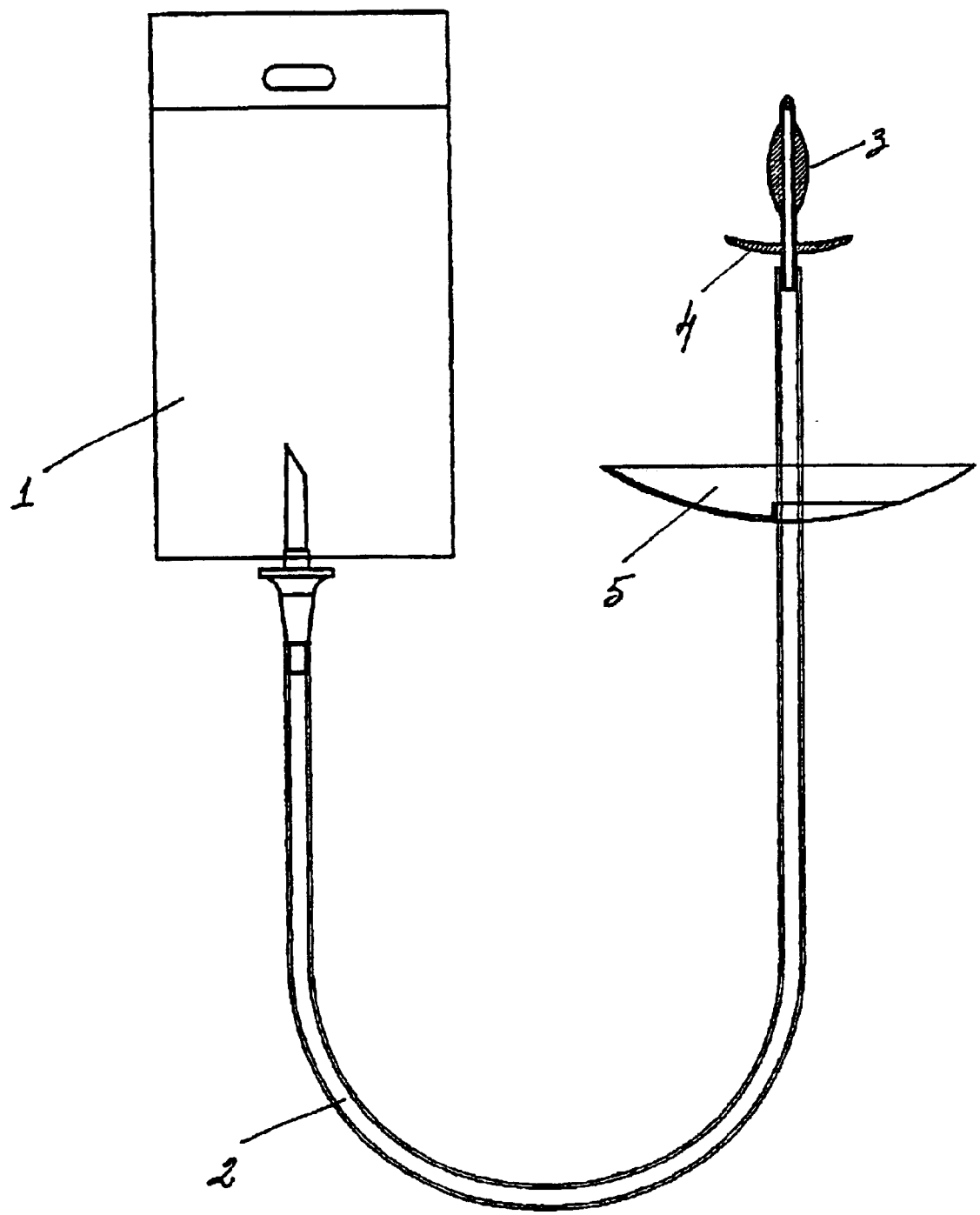
In FIG. 1 the device according to the present invention is illustrated.

The FIG. 1 schematically illustrates the device according to the present invention.

The FIGS. 2a, 2b and 2c represent a form of embodiment of the nozzle (3) of the present invention. Specifically, the FIG. 2a illustrates a view from above of the nozzle (3), with particular reference to the upper openings (9) which in this case are four and radially placed. The FIG. 2b represents a longitudinal section along the a—a plane of the nozzle (3) of the FIG. 2a, while the FIG. 2c illustrates a longitudinal section of the same nozzle, along the b—b plane, and the tongues (4) are visible only against the light.

The FIGS. 3a, 3b and 3c illustrate another form of embodiment of the nozzle (3). The FIG. 3a represents a view from above of this form of realization characterized in that the elongated egg-shaped body (6) has two inner cavities (10) suitable to impart greater flexibility to said body at the moment of the introduction into the anal channel through the sphincter. Said cavities (10) are also visible in the FIG. 3c which represents a longitudinal section along the b—b plane of the FIG. 3a. It is understood that this form of embodiment of the invention may also show only one cavity (10). Therefore the number of said cavities (10) is at least one.

The body (6) of the nozzle (3) having elongated egg-shaped conformation, has in its upper part (7) at least one opening (9), and in the lower portion it is linked up to each tongue (4) by the concave surface (8).

The particular elongated egg-shaped conformation of the body (6) has the nozzle (3) slided gently, not traumatically into the anal channel until the sphincter is in correspondence of the concave surface (8) linking up the lower portion of the body (6) with the tongues (4).

Holding tightly with the hands the bag (1) the pressure of the solution is increased until it is made to flow down inside the rectum. The increase of the pressure inside the rectum caused by the insertion of the solution would cause the undesirable emission of the nozzle (3). This is contrasted by its particular egg-shaped conformation which keeps in position the nozzle (3) and simultaneosly prevents the emission of the solution which is pushed by the bag. Therefore, the concave surface (8) represents the element suitable to house the anal sphincter and to keep the body of the nozzle (6) in the most appropriated position during the whole washing.

At the end of the operation, the nozzle (3) is extracted from the anal channel without disease for the user thanks to its elongated egg-shaped form.

In an alternative embodiment of the present invention, the body (6) has two opposed cavities (10) conferring a greater elasticity to the body itself, as well as a wider variation of size either at the moment of the introduction or of the extraction. In fact, according to this form of embodiment, at the moment of the introduction into the anal channel the body (6) is squeezed and this volume decrease makes its insertion easier to the notch (8) level; when inserted, the body (6) returns to its normal size suitable to create a catch to the expulsion of the nozzle (3) and a barrier to the emission of the washing solution.

The FIGS. 4a, 4b and 4c show, respectively, a view from below, a longitudinal section along the major axis (a) and a view from above of the disk or cup (5), optionally present in the device of the present invention, in its concave variation and removable from the tube (2). It consists of walls (11) along the channel (12) of insertion on the tube, and of a housing hole (13) for the tube itself.

The function of the disk or cup (5), optional in the device of the present invention, is to allow the downflow of the washing liquid without making the operator's hands dirty.

What is claimed is:

1. Device for rectal lavages consisting of a flexible container (1) containing the washing liquid, a flexible tube (2) and a nozzle (3), said nozzle having an inner channel and being equipped with an elongated egg-shaped body (6) from which an upper elongated portion (7) and a concave surface (8) depart, the upper portion (7) being equipped with at least one opening (9), and the concave surface (8) with two tongues (4) of slightly upwards curved shape, said elongated egg-shaped body (6) being further equipped with at least one cavity (10) not communicating with said inner channel and having an open end.

2. Device as claimed in claim 1 equipped with disk or cup (5) movable and smooth-running on the tube (2) and coaxial to it.

3. Device as claimed in claim 2 wherein the disk or cup (5) is removable from the tube (2).

* * * * *